(12) United States Patent
Salama et al.

(10) Patent No.: US 11,905,250 B2
(45) Date of Patent: Feb. 20, 2024

(54) METHODS FOR PREPARATION OF JASMONATE COMPOUNDS

(71) Applicant: Vidac Pharma Ltd., Jerusalem (IL)

(72) Inventors: Paul Salama, Ashdod (IL); Oren Menahem Becker, Mevasseret Zion (IL)

(73) Assignee: VIDAC PHARMA LTD., Rehovot (IL)

( * ) Notice: Subject to any disclaimer, the term of this patent is extended or adjusted under 35 U.S.C. 154(b) by 823 days.

(21) Appl. No.: 16/960,089

(22) PCT Filed: Jan. 6, 2019

(86) PCT No.: PCT/IL2019/050031
§ 371 (c)(1),
(2) Date: Jul. 6, 2020

(87) PCT Pub. No.: WO2019/135243
PCT Pub. Date: Jul. 11, 2019

(65) Prior Publication Data
US 2021/0078949 A1 Mar. 18, 2021

Related U.S. Application Data

(60) Provisional application No. 62/614,442, filed on Jan. 7, 2018.

(51) Int. Cl.
| | | |
|---|---|---|
| C07D 215/24 | (2006.01) | |
| C07C 57/03 | (2006.01) | |
| C07D 215/32 | (2006.01) | |
| C07C 17/357 | (2006.01) | |
| C07C 51/09 | (2006.01) | |
| C07C 51/41 | (2006.01) | |
| C07C 67/10 | (2006.01) | |
| C07C 67/303 | (2006.01) | |
| C07C 67/317 | (2006.01) | |
| C07C 67/32 | (2006.01) | |
| C07C 67/343 | (2006.01) | |
| C07C 67/475 | (2006.01) | |

(52) U.S. Cl.
CPC .......... *C07D 215/32* (2013.01); *C07C 17/357* (2013.01); *C07C 51/09* (2013.01); *C07C 51/412* (2013.01); *C07C 67/10* (2013.01); *C07C 67/303* (2013.01); *C07C 67/317* (2013.01); *C07C 67/32* (2013.01); *C07C 67/343* (2013.01); *C07C 67/475* (2013.01)

(58) Field of Classification Search
CPC ............................. C07D 215/24; C07C 57/03
USPC .......................................... 546/152; 562/504
See application file for complete search history.

(56) References Cited

U.S. PATENT DOCUMENTS

| 6,333,180 B1 | 12/2001 | Farbood et al. |
| 2013/0203689 A1 | 8/2013 | Ksshman et al. |

FOREIGN PATENT DOCUMENTS

| CN | 101001524 A | 7/2007 |
| CN | 102211993 A | 10/2011 |
| CN | 106083575 A | 11/2016 |
| JP | H03261743 A | 11/1991 |
| RU | 2195825 | 1/2003 |
| RU | 2198545 | 2/2003 |
| WO | WO 2007/066336 | 6/2007 |
| WO | WO 2007/066337 | 6/2007 |

OTHER PUBLICATIONS

International Search Report for PCT Application No. PCT/IL2019/050031 dated Mar. 25, 2019.
Johnson, F et al. (1982)—An efficient synthesis of methyl dl-cis-jasmonate—The Journal of Organic Chemistry, 47(22), 4254-4255.
Dang, H. T., Lee, Y. M., Kang, G. J., Yoo, E. S., Hong, J., Lee, S. M., . . . & Jung, J. H. (2012). In vitro stability and in vivo anti-inflammatory efficacy of synthetic jasmonates. Bioorganic & medicinal chemistry, 20(13), 4109-4116.
Lee, W. Y., Jang, S. Y., Kim, M., & Park, O. S. (1992). Synthetic Studies on Jasmonoids (II) 1: A New Synthesis Of Methyl dl-Jasmonate. Synthetic communications, 22(9), 1283-1291.
Liu, S., Wang, W. H., Dang, Y. L., Fu, Y., & Sang, R. (2012). Rational design and efficient synthesis of a fluorescent-labeled jasmonate. Tetrahedron Letters, 53(32), 4235-4239.
Torii, S., Tanaka, H., & Mandai, T. (1975). Electrolytic decarboxylation reactions. II. Syntheses of methyl dihydrojasmonate and methyl dl-jasmonate from 3-methoxycarbonyl-2-carboxynorbornane via anodic acetoxylation. The Journal of Organic Chemistry, 40(15), 2221-2224.
Zhao, Z., Xu, Y., Qian, Z., Tian, W., Qian, X., & Zhong, J. J. (2004). Novel fluoro-and hydroxyl-containing jasmonate derivatives as highly efficient elicitors in suspension cultures of Taxus chinensis. Bioorganic & medicinal chemistry letters, 14(18), 4755-4758.

*Primary Examiner* — Charanjit Aulakh
(74) *Attorney, Agent, or Firm* — Mark S. Cohen; PEARL COHEN ZEDEK LATZER BARATZ LLP

(57) ABSTRACT

This invention relates to methods for preparation of jasmonate compounds via a salt of jasmonic acid.

21 Claims, No Drawings

METHODS FOR PREPARATION OF JASMONATE COMPOUNDS

CROSS-REFERENCE TO RELATED APPLICATIONS

This application is a National Phase Application of PCT International Application Number PCT/IL2019/050031 filed on Jan. 6, 2019, which claims the benefit of U.S. Provisional Application Serial No. 62/614,442 filed Jan. 7, 2018, which is hereby incorporated by reference.

FIELD OF INVENTION

This invention relates to methods for preparation of jasmonate compounds via a salt of jasmonic acid.

BACKGROUND OF THE INVENTION

Jasmonates are a family of plant stress hormones, derived from linolenic acid by the octadecanoid pathway, which are found in minute quantities in many edible plants. Members of the jasmonate family include jasmonic acid and methyl jasmonate. These jasmonate compounds are crucial to intracellular signaling in response to injury and cause induction of a proteinase inhibitor that accumulates at low concentrations in response to wounding or pathogenic attacks. Recently it was shown that jasmonate compounds are directly cytotoxic for various types of human cancer cells derived from breast, prostate, skin, and blood cancers and have become attractive candidates as therapeutic agents for the treatment of cancers.

Conventional methods of manufacturing jasmonate derivatives involve toxic chemicals, tedious purification processes, and low purity and yields. Thus, it is desirable to develop a safer and simpler method for synthesizing jasmonate compounds in a high yield.

SUMMARY OF THE INVENTION

This invention relates to methods for preparation of jasmonate compounds via a salt of jasmonic acid.

In one aspect, the present invention is directed to a method of preparing a compound of formula (I)

(I)

wherein R is a heteroaryl group,
the method comprising
(a) treating jasmonic acid salt (9)

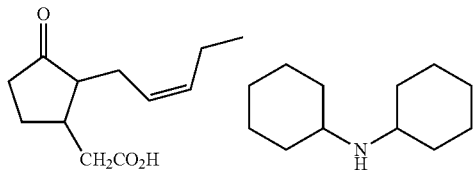
(9)

with an acid at a temperature of from about 0° C. to about 15° C. to provide compound (8),

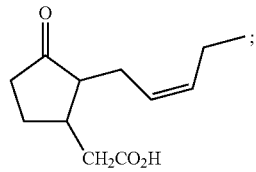
(8)

and
(b) reacting compound (8) with a hydroxylheteroaryl to provide the compound of formula (I).

In another aspect, the present invention is directed to a method of preparing jasmonic acid salt (9)

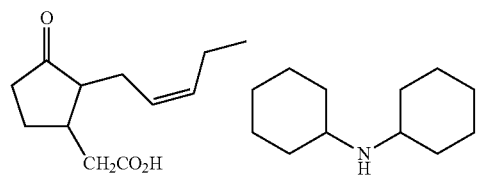
(9)

the method comprising
(a) hydrolyzing compound (6)

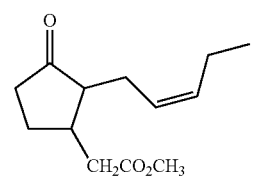
(6)

with a base at a temperature of from about 20° C. to about 30° C. to form a crude compound (8)

(8)

(b) reacting the crude compound (8) with dicyclohexylamine at a temperature of from about 0° C. to about 10° C. in an organic solvent to provide jasmonic acid salt (9).

DETAILED DESCRIPTION OF THE INVENTION

In one aspect, the present invention is directed to a method of preparing a compound of formula (I)

(I)

wherein R is alkyl, alkenyl, alkynyl, aryl, or heteroaryl, each optionally substituted with a group selected from alkyl, halo, nitro, CN, haloalkyl, aryl, heteroaryl, O-haloalkyl, OH, O-alkyl, SH, S-alkyl, $NH_2$, NH(alkyl), and $N(alkyl)_2$,
the method comprising
(a) treating jasmonic acid salt (9)

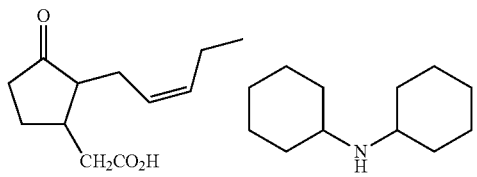
(9)

with an acid at a temperature of from about 0° C. to about 15° C. to provide Compound (8),

(8)

and
(b) reacting Compound (8) with a compound of ROH to provide the compound of formula (I).

In one aspect, the present invention is directed to a method of preparing a compound of formula (I)

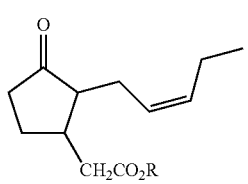
(I)

wherein R is a heteroaryl group,
the method comprising
(a) treating jasmonic acid salt (9)

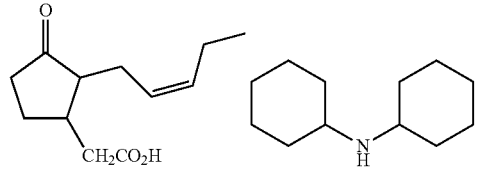
(9)

with an acid at a temperature of from about 0° C. to about 15° C. to provide compound (8),

(8)

(b) reacting compound (8) with a hydroxylheteroaryl to provide the compound of formula (I).

In some embodiments, the hydroxyheteroaryl of step (b) is optionally substituted with alkyl, halo, nitro, CN, haloalkyl, aryl, heteroaryl, O-haloalkyl, OH, O-alkyl, SH, S-alkyl, $NH_2$, NH(alkyl), and $N(alkyl)_2$.

In some embodiments, the hydroxyheteroaryl of step (b) is 8-hydroxyquinoline.

In some embodiments, the hydroxyheteroaryl of step (b) is 8-hydroxyquinoline, wherein said 8-hydroxyquinoline is optionally substituted with alkyl, halo, nitro, CN, haloalkyl, O-haloalkyl, aryl, heteroaryl, OH, O-alkyl, SH, S-alkyl, $NH_2$, NH(alkyl), and $N(alkyl)_2$.

In some embodiments, the compound of formula (I) is obtained with a yield of at least 99.0%

In some embodiments, in the method of the invention, R is a quinolinyl group.

In some embodiments, in the method of the invention, the temperature is from about 0° C. to about 10° C.

In some embodiments, in the method of the invention, the compound of formula (I) is obtained at a purity of about 99.0%. In some embodiments, the compound of formula (I) is obtained at a purity of about 99.6%. In other embodiments, the compound of formula (I) is obtained at a yield of about 94.9%. In some embodiments, the compound of formula (I) contains less than 5% of E isomer. In other embodiments, compound of formula (I) contains less than 4% of E isomer. In certain embodiments, the compound of formula (I) contains less than 3% of E isomer. In some embodiments, the compound of formula (I) is obtained with Z isomer in the amount of about 99.0%.

In some embodiments, in the method of the invention, jasmonic acid salt (9) is in the amount of about 110 g. In some embodiments, the acid used for the preparation of compound (8) is HCl in water.

In some embodiments, in the method of the invention, jasmonic acid salt (9) is prepared by (a) hydrolyzing a compound (6)

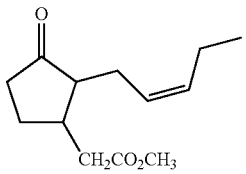
(6)

with a base to form a crude compound (8)

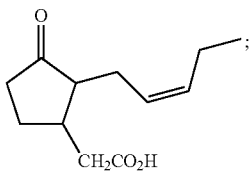
(8)

(b) reacting the crude compound (8) with dicyclohexylamine at a temperature of from about 0° C. to about 10° C. in an organic solvent to form jasmonic acid salt (9).

In some embodiments, in the method of the invention, the base is LiOH in water. In some embodiments, the organic solvent comprises ethyl acetate. In other embodiments, the organic solvent comprises heptane. In certain embodiments, the organic solvent is a mixture of ethyl acetate and n-heptane. In some embodiments, the ratio of the ethyl acetate and the n-heptane is about 1:3 in volume. In some embodiments, the hydrolyzing step (a) is conducted at a temperature from about 20° C. to about 30° C.

In some embodiments, in the method of the invention, the crude compound (8) is obtained at a purity of about 93.0%. In other embodiments, the crude compound (8) is obtained at a purity of about 94.0% or about 95%. In some embodiments, in the method for preparing compound (9), compound (6) is in an amount of about 110 g.

In some embodiments, in the method of the invention, compound (6) is prepared by treating compound (7)

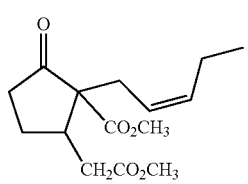
(7)

with LiCl in a solvent at a temperature of from about 120° C. to about 130° C.

In some embodiments, in the method of the invention, the solvent is a mixture of water and an organic solvent. In some embodiments, the organic solvent is DMF.

In some embodiments, in the method of the invention, compound (7) is prepared by reacting compound (4)

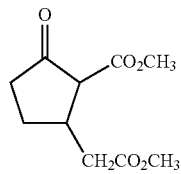
(4)

with 1-bromo-2-pentene in the presence of $Cs_2CO_3$.

In some embodiments, the compound of formula (I) is Compound (10)

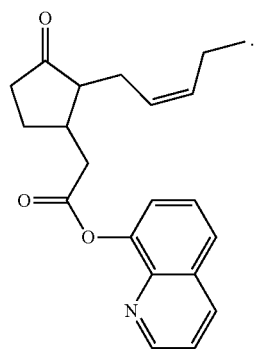
(10)

In another aspect, the present invention is directed to a method of preparing jasmonic acid salt (9)

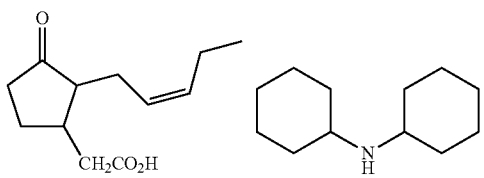
(9)

the method comprising
(a) hydrolyzing compound (6)

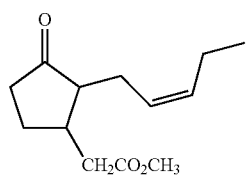
(6)

with a base to form a crude compound (8)

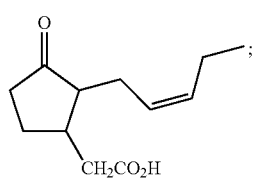
(8)

(b) reacting the crude compound (8) with dicyclohexylamine at a temperature of from about 0° C. to about 10° C. in an organic solvent to provide jasmonic acid salt (9).

In some embodiments, the base is LiOH in water. In some embodiments, the organic solvent comprises ethyl acetate. In other embodiments, the organic solvent comprises heptane. In some embodiments, the organic solvent is a mixture of ethyl acetate and n-heptane. In some embodiments, the ratio of the ethyl acetate and the n-heptane is about 1:3 in volume. In some embodiments, the hydrolyzing step (a) is conducted at a temperature from about 20° C. to about 30° C.

In some embodiments, the crude compound (8) is obtained at a purity of about 93.0%. In other embodiments, the crude compound (8) is obtained at a purity of about 94.0% or about 95.0%.

In some embodiments, compound (6) is prepared by treating compound (7)

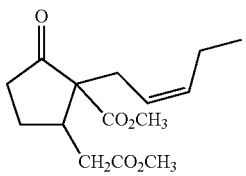

(7)

with LiCl in a solvent at a temperature of from about 120° C. to about 130° C. In some embodiments, the solvent is a mixture of water and an organic solvent. In some embodiments, the organic solvent is DMF. In some embodiments, in the method for preparing compound (6), compound (7) is in the amount of about 200 g.

In some embodiments, compound (7) is prepared by reacting compound (4)

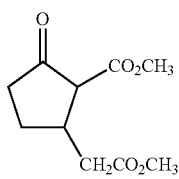

(4)

with 1-bromo-2-pentene in the presence of $Cs_2CO_3$. In some embodiments, compound (4) is in the amount of about 190 g.

In some embodiments, as used herein, the term "reacting" is meant to refer to the bringing together of the indicated reagents in such a way as to allow their molecular interaction and chemical transformation according to the thermodynamica and kinetics of the chemical system. Reacting can be facilitated, particularly for solid reagents, by using an appropriate solvent or mixture of solvents in which at least one of the reagents is at least partially soluble. Reacting is typically carried out for a suitable time and under conditions suitable to bring about the desired chemical transformation.

As used herein, an "alkyl" group refers to any saturated aliphatic hydrocarbon, including straight-chain and branched-chain alkyl groups. In one embodiment, the alkyl group has 1-4 carbons designated here as $C_1$-$C_4$-alkyl. In some embodiments, the alkyl group has 1-7 carbons designated here as $C_1$-$C_7$-alkyl. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

As used herein, the term "alkenyl" refers to an unsaturated monovalent chain of carbon atoms including at least one double bond, which may be optionally branched. It is understood that in embodiments that include alkenyl, illustrative variations of those embodiments include lower alkenyl, such as $C_2$-$C_6$, $C_2$-$C_4$ alkenyl, and the like.

As used herein, the term "alkynyl" refers to an unsaturated monovalent chain of carbon atoms including at least one triple bond, which may be optionally branched. It is understood that in embodiments that include alkynyl, illustrative variations of those embodiments include lower alkynyl, such as $C_2$-$C_6$, $C_2$-$C_4$ alkynyl, and the like.

The term "aryl" used herein alone or as part of another group denotes an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms.

In some embodiments, a "heteroaryl" group refers to an aromatic heterocycle having at least one heteroatom ring member such as sulfur, oxygen, or nitrogen. Heteroaryl groups include monocyclic and polycyclic (e.g., having 2, 3 or 4 fused rings) systems. Any ring-forming N atom in a heteroaryl group can also be oxidized to form an N-oxo moiety. Examples of heteroaryl groups include without limitation, pyridyl, N-oxopyridyl, pyrazinyl, furyl, quinolinyl, isoquinolyl, thienyl, imidazolyl, indolyl, benzofuryl, indazolyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

In some embodiments, the terms "jasmonic acid salt (9)," "Compound (9) (salt)," and "Compound (9)" are used interchangeably.

As used herein, the terms "hydroxylheteroaryl" and "hydroxyheteroaryl" are used interchangeably.

As exemplified in Scheme 1, a compound of formula (I) can be prepared from commercially available compounds via 10 steps. Compound (3) can be obtained based on the reaction procedures known in the art (e.g., J. Org. Chem., 1982, 47(22), 4254-4255). Reduction of Compound (3) affords Compound (4), followed by reacting with (Z)-1-bromo-2-pentene to give Compound (7). Treatment of Compound (7) with LiCl gives Compound (6). Compound (6) can be purified by methods known in the art, such as distillation or column chromatography. Hydrolysis of Compound (6) leads to a crude Compound (8). The crude Compound (8), without further purification, can react with dicyclohexylamine to produce Compound (9) (jasmonic acid salt (9)), a dicyclohexylamine salt of Compound (8). Subsequently, the obtained pure Compound (8) by neutralizing Compound (9) can react with 8-hydroxyquinoline to give Compound (10).

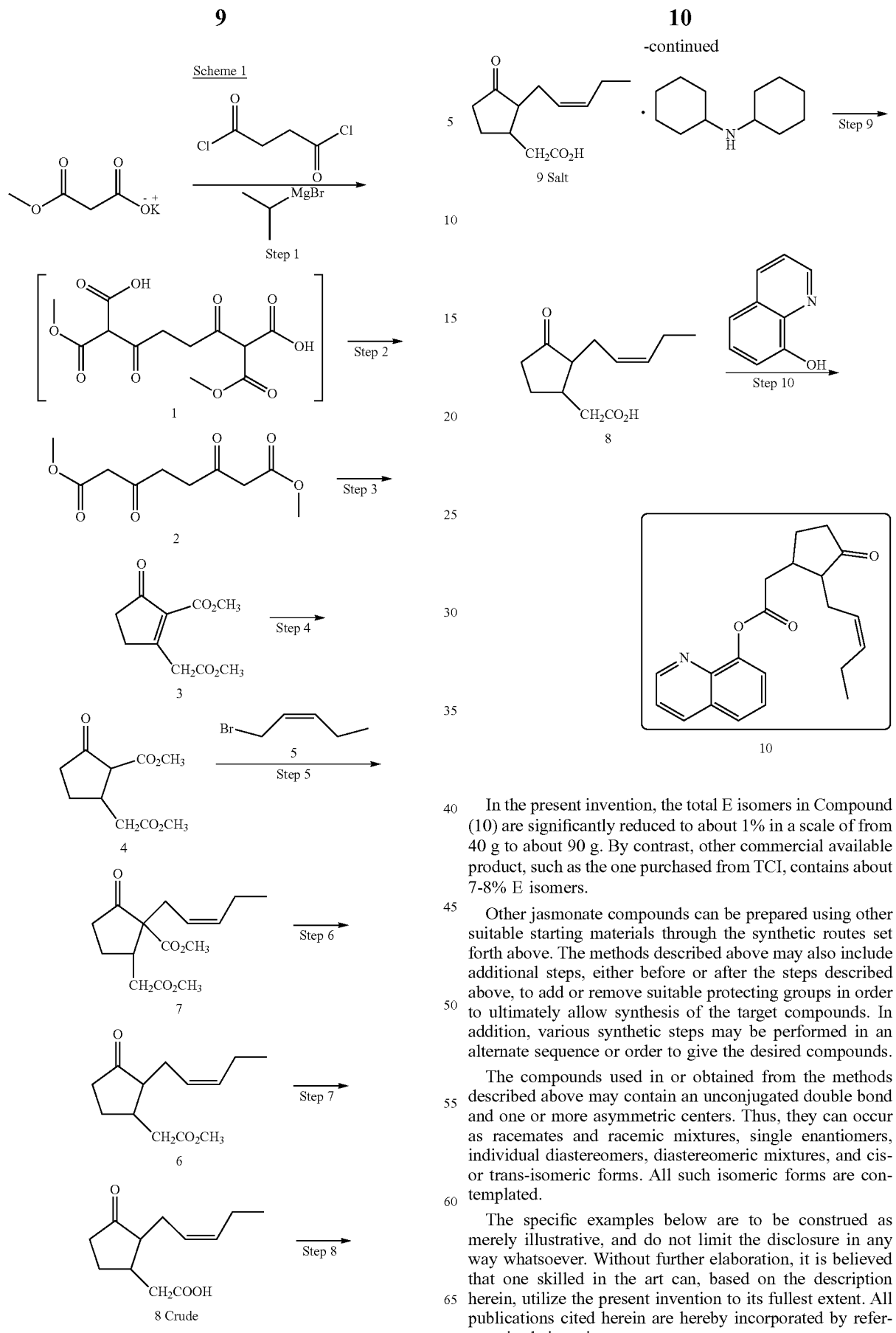

Scheme 1

In the present invention, the total E isomers in Compound (10) are significantly reduced to about 1% in a scale of from 40 g to about 90 g. By contrast, other commercial available product, such as the one purchased from TCI, contains about 7-8% E isomers.

Other jasmonate compounds can be prepared using other suitable starting materials through the synthetic routes set forth above. The methods described above may also include additional steps, either before or after the steps described above, to add or remove suitable protecting groups in order to ultimately allow synthesis of the target compounds. In addition, various synthetic steps may be performed in an alternate sequence or order to give the desired compounds.

The compounds used in or obtained from the methods described above may contain an unconjugated double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated.

The specific examples below are to be construed as merely illustrative, and do not limit the disclosure in any way whatsoever. Without further elaboration, it is believed that one skilled in the art can, based on the description herein, utilize the present invention to its fullest extent. All publications cited herein are hereby incorporated by reference in their entirety.

EXAMPLES

Example 1: Synthesis of Dimethyl 3,6-Dioxooctanedioate (Compound (2))

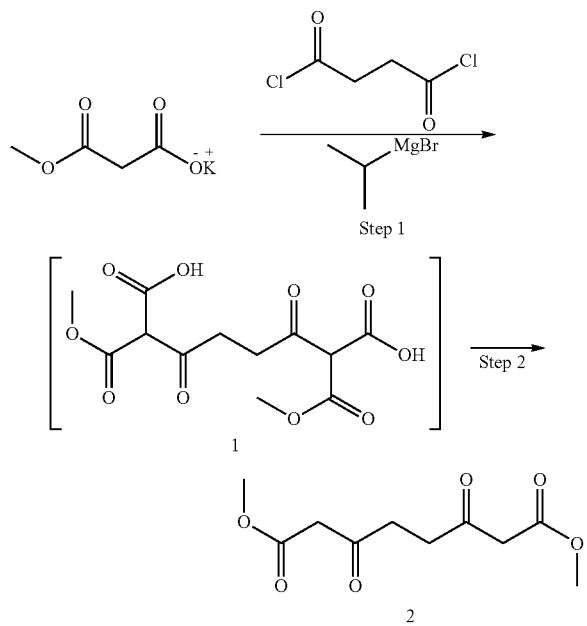

I$_2$ (6.5 g) and the solution of 2-bromopropane (2063 g) in THF (9.0 L) were added into THF (9.0 L) and Mg (408 g, 16.78 mol) at 50° C. under nitrogen protection. The reaction was heated to reflux for 2 hr. The reaction mixture was cooled to room temperature and THF (14.5 L) was added. Potassium 3-methoxy-3-oxopropanoate (2620 g, 16.78 mol) was added in portions. The reaction was heated to reflux for 1 hr then cooled to room temperature. Succinyl chloride (1240 g, 8.0 mol) was then slowly added and the medium was stirred overnight. 10% H$_2$SO$_4$ was added to adjust pH to 1~2. The mixture was extracted with ethyl acetate (6.5 L×2). The combined organic phase was washed with aq. NaHCO$_3$ and brine. The organic phase was concentrated to give oil (1159 g). This oil product was used in next step without any further purification. $^1$H-NMR (CDCl$_3$/TMS) δ 2.864 (s, 4H, CH$_2$), 3.527 (s, 4H, CH$_2$), 3.649 (m, 6H, CH$_3$). Calculated Mass: 230.079 M+Na=253.16.

Example 2: Synthesis of Methyl 2-(2-Methoxy-2-Oxoethyl)-5-Oxocyclopent-1-Enecarboxylate (Compound (3))

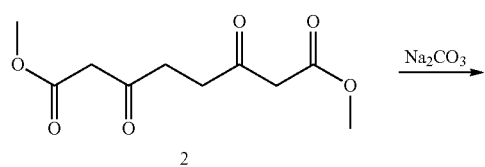

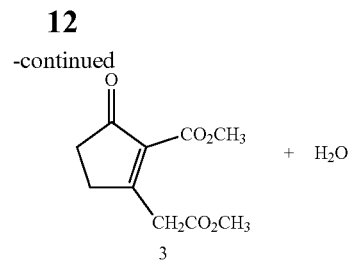

Dimethyl 3,6-dioxooctanedioate (Compound (2), 965.5 g, 4.19 mol) and Na$_2$CO$_3$ (533.5 g, 5.03 mol) were added to water (4340 mL). Concentrated HCl was added to adjust pH to 1~2. The mixture was filtered and the filter cake was washed with water. The mother liquor was extracted with ethyl acetate (1930 mL×3). The filter cake was dissolved in combined organic phase and the organic phase was concentrated. Then n-heptane (2500 ml) was added. The mixture was filtered and the cake was washed with n-heptane and dried to give solid (545 g). Yield is 61.2%. Purity is 97.3% (HPLC). $^1$H-NMR (CDCl$_3$/TMS) δ 2.543~2.568 (m, 2H, CH$_2$), 2.796~2.821 (m, 2H, CH$_2$), 3.748 (s, 3H, CH$_3$), 3.853 (s, 3H, CH$_3$), 3.887 (s, 2H, CH$_2$). Calculated Mass: 212.068 M+Na=235.18.

Example 3: Synthesis of Methyl 2-(2-Methoxy-2-Oxoethyl)-5-Oxocyclopentanecarboxylate (Compound (4))

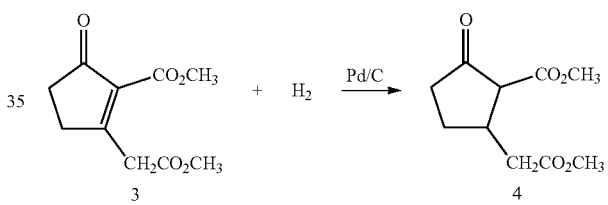

The mixture of MeOH (1.2 L), methyl 2-(2-methoxy-2-oxoethyl)-5-oxocyclopent-1-enecarboxylate (Compound (3), 150 g, 0.707 mol) and 5% Pd/C wet (15 g) was stirred at room temperature under 0.4~0.5 mPa of hydrogen for 6~7 hrs. The mixture was filtered and the filter cake was washed with MeOH. The filtrate was concentrated to give oil (152 g). The oil product was used directly in the next step without any further purification. $^1$H-NMR (CDCl$_3$/TMS) δ 2.353~2.558 (m, 6H, CH$_2$, CH), 2.993 (s, 2H, CH$_2$), 3.671 (s, 3H, CH$_3$), 3.757 (s, 3H, CH$_3$).

Example 4: Synthesis of (Z)-1-Bromopent-2-Ene (Compound (5))

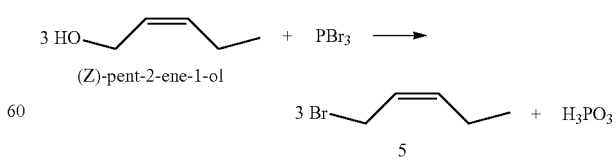

The solution of PBr$_3$ (92.4 g, 0.34 mol) in MTBE (84 ml) was added dropwise to the mixture of (Z)-pent-2-en1-ol (84.0 g, 0.98 mol) and MTBE (420 mL) under N$_2$ protection at 0~10° C. The mixture was stirred at room temperature for 1~2 hrs. Aqueous NaHCO$_3$ was added to adjust pH to 6~7. The aqueous phase was extracted with MTBE (168 ml). The combined organic phase was washed with brine. The organic phase was used directly in the next stage without any further purification. $^1$H-NMR (CDCl$_3$/TMS) δ 1.001 (m, 3H, CH$_3$), 2.120~2.157 (m, 2H, C$_2$) 3.972~3.992 (d, J=8 Hz, 2H, CH$_2$), 5.568~5.690 (i, 2H, CH=CH).

Example 5: Synthesis of (Z)-Methyl 2-(2-Methoxy-2-oxoethyl)-5-Oxo-1-(Pent-2-en-1-yl) Cyclopentane Carboxylate (Compound (7))

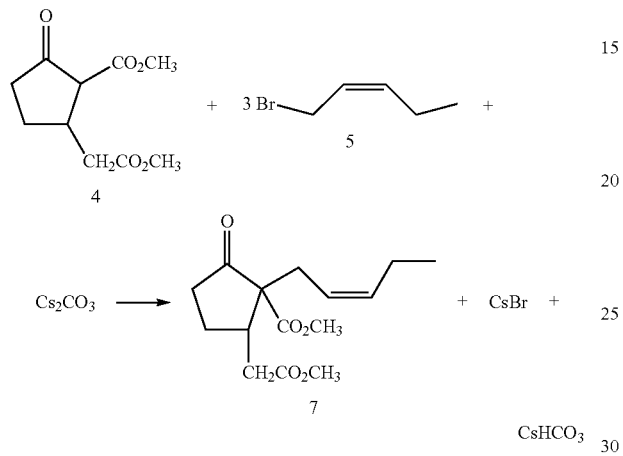

The solution of (Z)-1-bromopent-2-ene (Compound (5)) in MTBE in last step was added dropwise into the mixture of Methyl 2-(2-methoxy-2-oxoethyl)-5-oxocyclopentanecarboxylate (Compound (4), 190 g, 0.88 mol), MTBE (950 mL), Cs$_2$CO$_3$ (303.4 g, 0.93 mol), and tetrabutylammonium bromide (19.0 g) at 0° C. under N$_2$ protection. The mixture was stirred at room temperature for 4~5 hrs. The mixture was filtered and washed with water. The organic phase was concentrated to give oil (256 g). $^1$H-NMR (CDCl$_3$/TMS) δ 0.914~0.955 (m, 3H, CH$_3$), 1.726~1.829 (m, 1H, CH), 2.000~2.250 (m, 5H, CH$_2$, CH), 2.501~2.712 (m, 5H, CH$_2$, CH), 3.674~3.678 (m, 6H, CH$_3$), 5.102~5.149 (m, 1H, CH), 5.491~5.555 (m, 1H, CH).

Example 6: Synthesis of (Z)-Methyl 2-(3-Oxo-2-(Pent-2-en-1-yl)cyclopentyl)acetate (Compound (6))

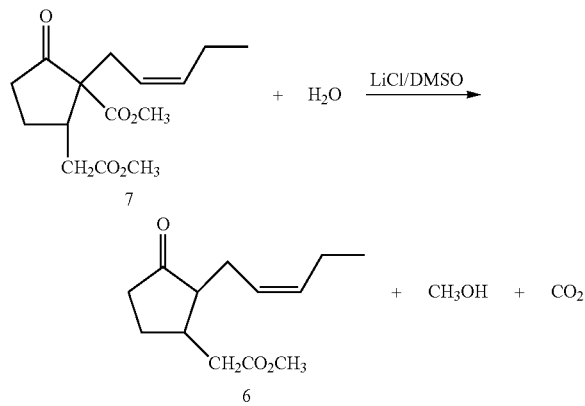

The mixture of (Z)-methyl 2-(2-methoxy-2-oxoethyl)-5-oxo-1-(pent-2-en-1-yl) cyclopentane carboxylate (Compound (7), 209 g, 0.74 mol), LiCl (62.8 g, 1.48 mol), water (26.6 g, 1.48 mol) and DMF (627 mL) was heated to 120-130° C. for 9~10 hrs. The mixture is cooled to room temperature and water (2.09 L) and ethyl acetate (1.04 L) was added. The ethyl acetate phase was washed with brine and concentrated. The residue was distilled at 1~2 mmHg to collect 120-130° C. fraction to give light yellow oil (115 g). Purity is 81.9% (GC) and yield is 69%. $^1$H-NMR (CDCl$_3$/TMS) δ 0.933~0.971 (t, d=7.6 Hz, 3H, CH$_3$), 1.434~1.538 (m, 1H, CH), 1.874~2.393 (m, 10H, CH$_2$), 2.671~2.740 (m, 1H, CH), 3.691 (s, 3H, CH$_3$), 5.219~5.297 (m, 1H, CH), 5.417~5.481 (m, 1H, CH).

Example 7: Synthesis of (Z)-2-(2-(But-2-en-1-yl)-3-Oxocyclopentyl)Acetic acid (Crude Compound (8))

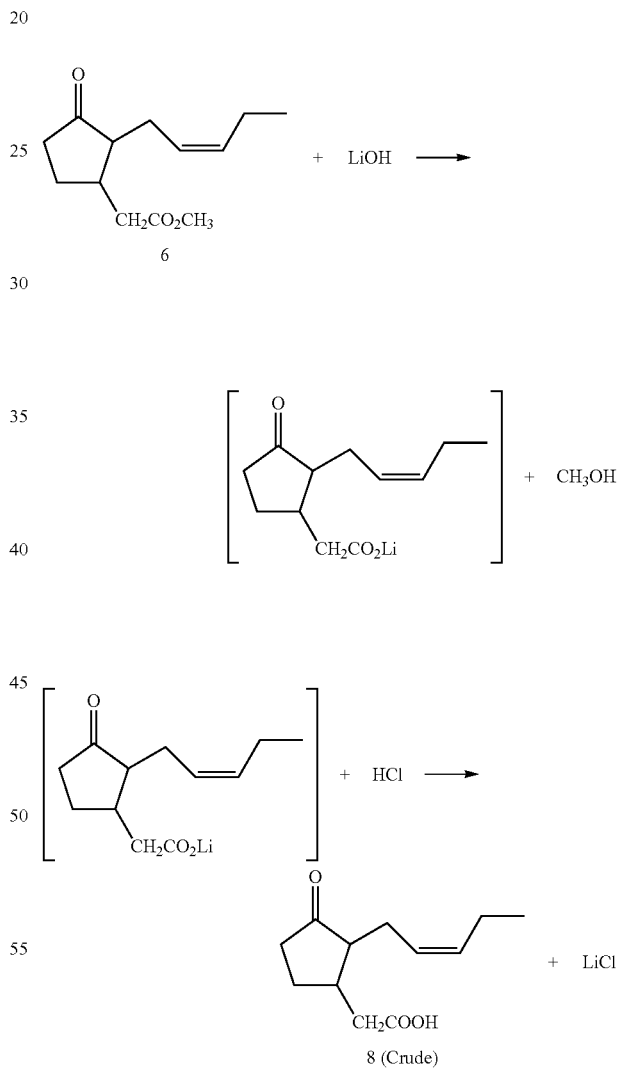

The mixture of (Z)-methyl 2-(3-oxo-2-(pent-2-en-1-yl)cyclopentyl)acetate (Compound (6), 113 g, 0.5 mol), water (565 mL), LiOH.H$_2$O (31.7 g, 0.76 mol) was stirred at room temperature for 2.5~3 hrs. Dichloromethane (339 mL) was added. Aqueous HCl was added to adjust pH to 2~3. The organic phase was concentrated to give crude oil (105 g).

Example 8: Synthesis of Dicyclohexylamine (Z)-2-(3-Oxo-2-(pent-2-en-1-yl)cyclopentyl)acetate (Compound (9))

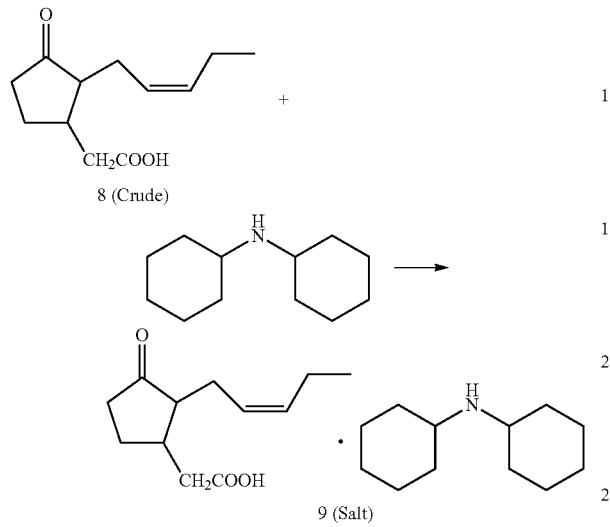

Dicyclohexylamine (99.7 g, 0.55 mol) was added drop wise to the mixture of (Z)-2-(2-(but-2-en-1-yl)-3-oxocyclopentyl)acetic acid (Compound (8), 105 g, 0.5 mol), ethyl acetate (263 mL) and n-heptane (788 mL) at 0~10° C. and stirred for 2~3 hrs. The mixture was filtered. The filter cake was recrystallized with ethyl acetate (315 mL), isopropanol (105 mL) and n-Heptane (630 mL) to give off-white solid (134 g). Yield was 68.5%. $^1$H-NMR (CDCl$_3$/TMS) δ 0.933~0.961 (t, d=7.6 Hz, 3H, CH$_3$), 1.128~1.261 (m, 6H, CH$_2$), 1.333~1.423 (m, 4H, CH$_2$), 1.465~1.568 (m, 1H, CH), 1.634~1.662 (m, 2H, CH$_2$), 1.767~1.799 (m, 4H, CH$_2$), 1.917~2.609 (m, 15H, CH$_2$, CH), 2.851~2.907 (s, 2H, CH$_2$), 5.304~5.421 (m, 2H, CH=CH), 7.928~7.936 (bs, 2H, OH, NH).

Example 9: Synthesis of (Z)-2-(3-Oxo-2-(pent-2-en-1-yl)cyclopentyl)acetic acid (Compound (8))

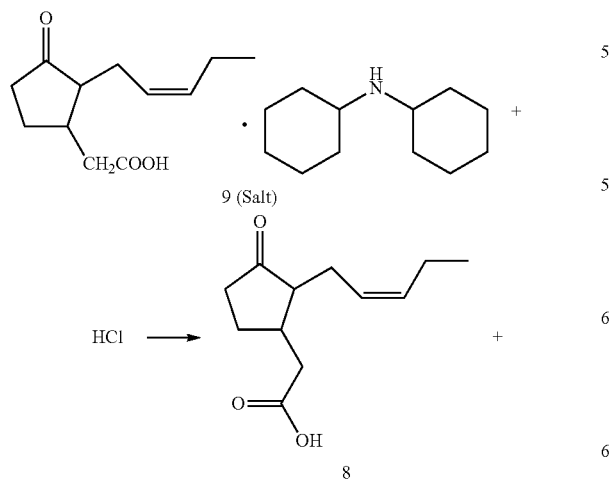

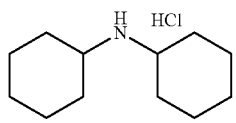

Concentrated HCl (33.5 ml, 0.34 mol) in water (360 ml) was added drop-wise to the mixture of dicyclohexylamine (Z)-2-(3-oxo-2-(pent-2-en-1-yl)cyclopentyl) acetate (Compound (9), 110 g, 0.28 mol) and dichloromethane (550 mL) at 0~15° C. and stirred for 1~2 hrs. The mixture was filtered. The organic phase was washed with water and brine, dried with MgSO$_4$ to give a Compound (8) solution that was used directly in the next step. $^1$H-NMR (CDCl$_3$/TMS) δ 0.919~0.957 (t, d=7.6 Hz, 3H, CH$_3$), 1.475~1.531 (m, 1H, CH), 1.887~2.401 (m, 10H, CH$_2$), 2.742~2.771 (m, 1H, CH), 5.223~5.250 (m, 1H, CH), 5.432~5.459 (m, 1H, CH).

Example 10: Synthesis of (Z)-Quinolin-8-yl-2-(3-oxo-2-(pent-2-en-1-yl)cyclopentyl)acetate (Compound (10))

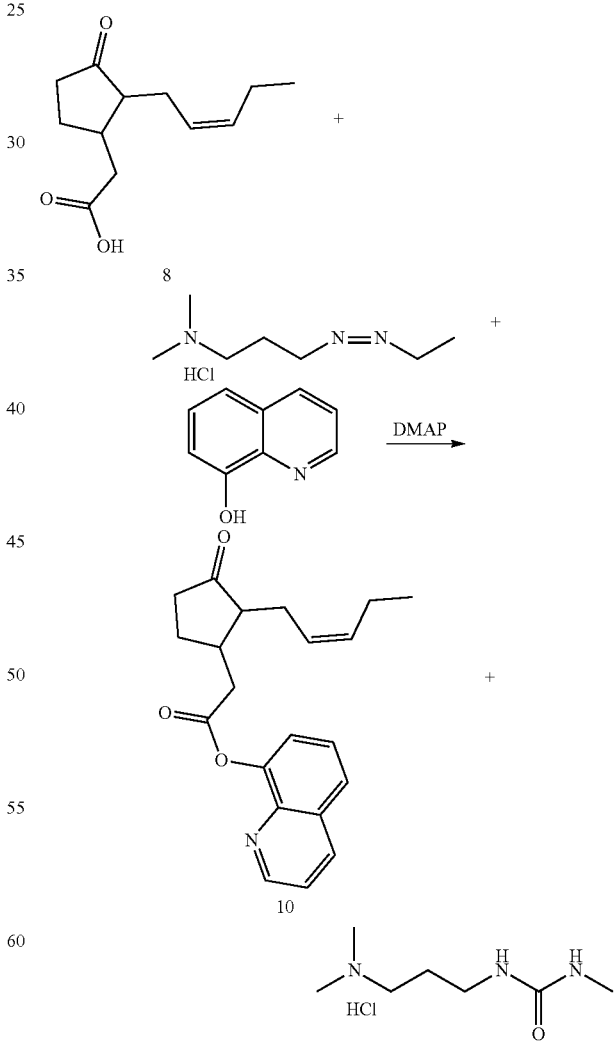

EDCI.HCl (59.4 g, 0.31 mol), 8-hydroxyquinoline (44.8 g, 0.31 mol) and DMAP (1.7 g, 0.014 mol) were added into the solution of (Z)-2-(3-oxo-2-(pent-2-en-1-yl)cyclopentyl) acetic acid (Compound (8)) in DCM in last step. The mixture was stirred at room temperature for 3 hrs. Concentrated HCl (15.2 g) in water (300 ml) was added. The organic phase was extracted with DCM (236 ml). The combined organic phase was washed with water and was adjusted to pH 5-6 by aq. NaHCO$_3$. The organic phase was washed with brine, water and dried with MgSO$_4$. The mixture was filtered and the filtrate was concentrate to give light yellow oil (89.9 g). Yield was 94.9%. Chemical purity was 99.6% and the Z isomer was 99.06%. $^1$H-NMR (CDCl$_3$/TMS) δ 0.953~0.990 (t, d=7.2 Hz, 3H, CH$_3$), 1.751~2.533 (m, 10H, CH$_2$), 2.760~2.820 (m, 1H, CH), 3.155~3.204 (m, 1H, CH), 5.346~5.502 (m, 2H, CH=CH), 7.388~7.441 (m, 2H, ArH), 7.500~7.539 (m, 1H, ArH), 7.697~7.720 (m, 1H, ArH), 8.139~8.163 (m, 1H, ArH), 8.855~8.866 (m, 1H, ArH).

Example 11: Observation of Salt Formation Conditions

Example 11a: Sodium Salt Formation

Reactions were conducted to form sodium salts under the conditions as described in Table 1. The sodium salt was observed. No good solid was obtained. Crude compound 8 was a transient intermediate which was not isolated in the reaction. In some embodiments, the unit "v" used herein refers to the number of volumes of solvent or others in liquid form used in a reaction.

TABLE 1

Sodium Salt Formation

| Lot No. | Method | Solvents | Result |
| --- | --- | --- | --- |
| 1 | t-BuONa 1 eq. | Add to ethyl acetate 10 v | Clear solution |
| 2 | Ethanol 2 v. | Add to isopropyl acetate 10 v | Clear solution |
| 3 | The sodium salt solution was added dropwise to solvents | Add to heptane 10 v | Oil product |
| 4 | | Add to MTBE 50 v | A little solid was precipitated, but oil product was obtained by filtration. |

Example 11b: Other Salt Formation

Reactions were conducted to form a variety of salts as described in Table 2. White solid precipitate was obtained by treating distilled Compound (6) with dicyclohexylamine, which could further be recrystallized with ethyl acetate. However, when the crude Compound (6) with ~65% purity was used to react with dicyclohexylamine, it was difficult to form the salt.

TABLE 2

Salt Formation Observation

| Lot No. | Base/Solvent | Result | Source of starting material (MJ) |
| --- | --- | --- | --- |
| 1 | EtONa 1 eq. MTBE 10 v 0~10° C. | No solid precipitate. Concentrate to dryness give oil product | Compound (6) From TCI supplier |
| 2 | t-BuOK 1 eq. MTBE 10 v 0~10° C. | No solid precipitate. Concentrate to dryness give oil product | |
| 3 | Trinpropylamine 1 eq. MTBE 10 v 0~10° C. | No solid precipitate. Concentrate to dryness give oil product | |
| 4 | n-Butylamine 1 eq. MTBE 10 v 0~10° C | No solid precipitate. Concentrate to dryness give oil product | |
| 5 | Cyclohexaneamine 1 eq. MTBE 10 v 0~10° C. | No solid precipitate. Concentrate to dryness give oil product | |
| 6 | Benzylamine 1 eq. MTBE 10 v 0~10° C. | No solid precipitate. Concentrate to dryness give oil product | |
| 7 | t-Butyl amine 1 eq. MTBE 10 v 0~10° C. | No solid precipitate. Concentrate to dryness give oil product | |
| 8 | Dimehtyl ethylenediamine 1 eq. MTBE 10 v 0~10° C. | No solid precipitate. Concentrate to dryness give oil product | |
| 9 | Ethanediamine 1 eq. MTBE 10 v 0~10° C. | White solid precipitate, but very hygroscopic during filtration | |
| 10 | Ethanediamine: 0.6 eq EA: 2.5 V | N/A | |
| 11 | Dicyclohexylamine 1 eq. MTBE 10 v 0~10° C. | Good white solid precipitate | |
| 12 | Dicyclohexylamine 1 eq. Ethyl acetatre 10 v 0~10° C. | No solid precipitate. Concentrate to dryness give oil product | Crude Compound (6) (~65% purity MHQ-25-106-1) |
| 13 | Dicyclohexylamine 1 eq. Ethyl acetatre 10 v 0~10° C. | White solid with 65% yield | Distilled Compound (6) (~80% purity, MHQ-25-117-1) |
| 14 | Dicyclohexylamine 1 eq. Ethyl acetatre 10 v 0~10° C. | Crystallize once with ethyl acetate, overall yield ~36% | Distilled Compound (6) (~80% purity MHQ-25-117-1) |

Example 11c: Formation of Dicyclohexylamine Salt (9)

Table 3 provides experimental conditions to form the dicyclohexylamine salt (9) with crude Compound (8). After further optimization, the purity of crude Compound (6) was improved from ~65% to ~85%. With crude Compound (6) (~85% purity), the salt was obtained directly.

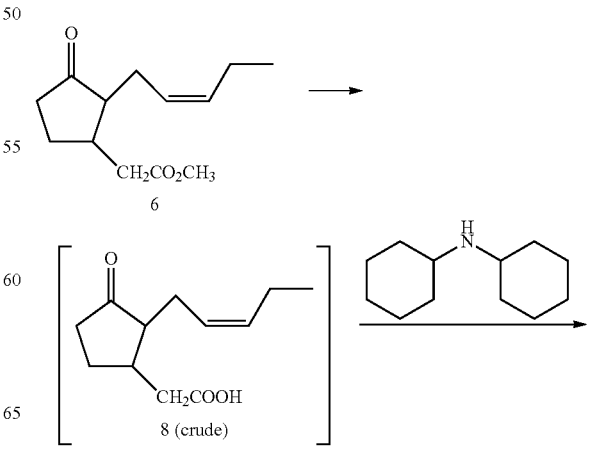

-continued

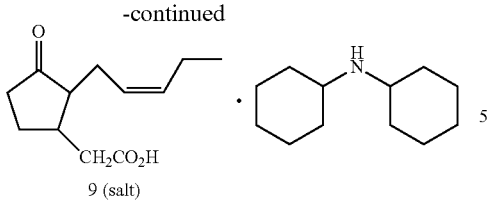

9 (salt)

TABLE 3

Preparation of Compound (9) (salt) with crude Compound (6)

| Batch No. | Scale | Yield | Purity (by GC) |
|---|---|---|---|
| 1 | Compound (6) crude ~90%: 0.8 g<br>Dicyclohexylamine: 1.0 eq<br>EA: 5 V<br>n-heptane: 10 V | 45% | 95.6% + 1.36%<br>(cis-cis isomer) = 96.9% |
| 2 | Compound (6) crude ~85%: 4 g<br>Dicyclohexylamine: 1.0 eq<br>EA: 2 V<br>n-heptane: 6 V | 48% | 95.19% + 0.64%<br>(cis-cis isomer) = 95.83% |
| 3 | Compound (6) crude ~83%: 21 g<br>Dicyclohexylamine: 1.0 eq<br>EA: 2.5 V<br>n-heptane: 5 V | 55% | 88.18% + 5.88%<br>(cis-cis isomer) = 94.08% |

Example 11d: Purification of Salt

Table 4 provides the experiments to purify Compound (9) (salt). Among the recrystallization conditions, a mixture of the ethyl acetate/heptane provided better recrystallization results.

TABLE 4

Purification of Compound (9) (salt)

| Batch No. | Solvent for re-crystallization | Yield | Purity of Compound (9) (salt) |
|---|---|---|---|
|  | Compound (9) Salt crude |  | 88.18% |
| 1 | EA (5 vol)/Heptane (15 vol) | 86% | 90.20% |
| 2 | EA (3 vol)/IPA (1 vol) | 90% | 85.07% |
| 3 | MeOH (0.5 vol)/Water (4 vol) | 50% | 86.25% |
| 4 | Water (4 vol)/95% EtOH (0.5 vol) | 67% | 86.08% |
| 5 | Water (4 vol)/95% IPA (0.5 vol) | 63% | 86.01% |

Example 12: Preparation of Compound (10) with Purified Compound (9) (Salt)

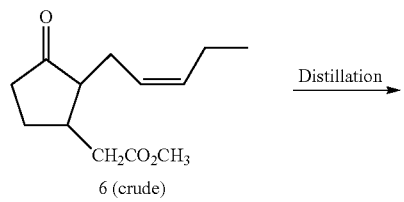

6 (crude)

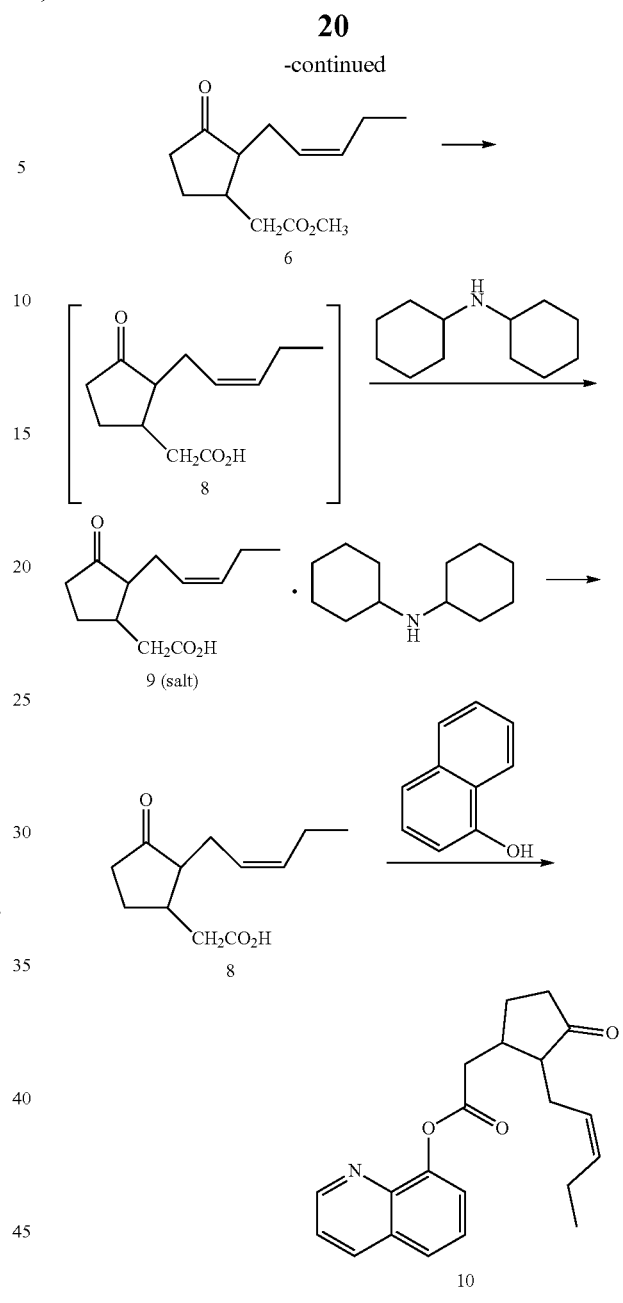

Although the crude Compound (8) (~85% purity) can form salt directly, distillation of Compound (8) was still necessary. It was found that for compound 9 (salt) that was formed from crude compound 6 without distillation and then carried out to the final API Compound 10, some impurities were found in compound 10 compared to the reference sample before (compound 6 purchased from TCI).

Purification of crude compound 6 for optimal purity comprises the following steps: (i) distillation of the crude compound 6 under vacuum; (ii) salt formation with dicyclohexylamine (DCHA) to form compound 9 (salt); (iii) recrystallization of compound 9 (salt); and acidification to compound (8). It was found that the chemical purity of compound 10 was improved from 93% to ~99% VS ~97% by compound 6 from TCI) and the total E isomers can be significantly reduced. They were about 2~3% VS 7-8% by compound 6 from TCI). The results are provided in Table 5.

TABLE 5

Summary of the Impurity Profile for Compound (10) in Different Batches

| Batch No. | Note | Compound (10) RT17.5 (min) | ImpA RT 18.5 | RRT1.07 RT 18.8 | RRT1.08 RT 19.0 | RT 18.2 (min) | RT 20.3 (min) | RT 20.4 (min) |
|---|---|---|---|---|---|---|---|---|
| 1 | Reference standard Starting material from TCI | 97.56% | 0.58% | 0.51% | 0.71% | ND | ND | ND |
| 2 | Compound (6) from TCI | 98.1% | 0.55% | 0.33% | 0.46% | 0.31% | ND | ND |
| 3 | Purification of Compound (6) with distillation and salt formation, then recrystallization (two times) | 99.1% | ND | 0.05% | ND | 0.36% | ND | ND |
| 4 | Purification of Compound (6) with distillation and salt formation, then recrystallization (one time) | 98.9% | ND | ND | ND / ND | 0.28% | ND | 0.11% |
| 5 | Purification of Compound (6) with distillation and salt formation | 97.9% | ND | ND | ND | 0.42% | 0.36% | 0.71% |
| 6 | Distilled products (Compound (6)) as raw material Without salt formation and recrystallization | 97.05% | 0.09% | ND | ND | 0.43% | 0.47% | 0.91% |
| 7 | Without distillation Purification of Compound (6) with salt formation, then recrystallization (MeOH, 0.5 vol/water, 4 vol) | 97.14% | 0.05% | ND | ND | 0.35% | ND | ND |
| 8 | Without distillation Purification of Compound (6) with salt formation, then recrystallization (95% EtOH, 0.5 vol/water, 4 vol) | 97.07% | 0.05% | ND | ND | 0.35% | 0.07% | 0.11% |
| 9 | Without distillation Purification of Compound (6) with salt formation, then recrystallization (IPA, 0.5 vol/water, 4 vol) | 96.9% | ND | 0.03% | ND | 0.35% | ND | ND |
| 10 | Without distillation and recrystallization Purification of Compound (6) with salt formation | 92.5% | ND | 0.06% | ND | 0.27% | 0.50% | 1.01% |

| Batch No. | Note | RT 25.7 (min) | RT 25.8 (min) | RT 26.5 (min) | RT 27.3 (min) | RT 27.8 (min) | RT 28.3 (min) | RT 28.8 (min) |
|---|---|---|---|---|---|---|---|---|
| 1 | Reference standard Starting material from TCI | ND | 0.09% | ND | 0.05% | ND | ND | ND |
| 2 | Compound (6) from TCI | ND | ND | ND | 0.04% | ND | ND | ND |
| 3 | Purification of Compound (6) with distillation and salt formation, then | ND | ND | ND | ND | ND | 0.09% | 0.1% |

TABLE 5-continued

Summary of the Impurity Profile for Compound (10) in Different Batches

| | | | | | | | | |
|---|---|---|---|---|---|---|---|---|
| | recrystallization (two times) | | | | | | | |
| 4 | Purification of Compound (6) with distillation and salt formation, then recrystallization (one time) | ND | ND | ND | 0.04% | 0.04% | 0.04% | 0.07% |
| 5 | Purification of Compound (6) with distillation and salt formation | 0.03% | 0.03% | 0.09% | 0.05% | 0.12% | 0.05% | 0.06% |
| 6 | Distilled products (Compound (6)) as raw material Without salt formation and recrystallization | ND | 0.08% | 0.12% | 0.07% | 0.11% | 0.04% | 0.05% |
| 7 | Without distillation Purification of Compound (6) with salt formation, then recrystallization (MeOH, 0.5 vol/ water, 4 vol) | 0.06% | ND | 0.12% | 0.08% | 1.0% | 0.57% | 0.68% |
| 8 | Without distillation Purification of Compound (6) with salt formation, then recrystallization (95% EtOH, 0.5 vol/ water, 4 vol) | 0.09% | ND | 0.20% | 0.20% | 0.90% | 0.38% | 0.51% |
| 9 | Without distillation Purification of Compound (6) with salt formation, then recrystallization (IPA, 0.5 vol/ water, 4 vol) | 0.06% | ND | 0.11% | 0.13% | 0.88% | 0.49% | 0.61% |
| 10 | Without distillation and recrystallization Purification of Compound (6) with salt formation | 0.31% | ND | 0.54% | 0.54% | 1.40% | 0.73% | 0.68% |

Compared to the reference sample, two groups of unknown impurities with RT 18.0~25.4 min and RT 26.2~28.5 min were found. These impurities from Compound (6) are difficult to be removed by forming Compound (9) (salt) and recrystallization of the Compound (9) (salt). Thus, distillation of Compound (6) crude under vacuum is still necessary. The chemical purity of Compound (10) was improved from 93% to ~99% when distilled Compound (6) was used.

Example 13: Comparison of Z Isomer of Compound (10) from Different Batches

Table 6 provides data showing that Z/E ratio was significantly improved (total E-isomer 2~3%) in comparison with a reference sample with Compound (6) from TCI (total E-isomer ~7%).

TABLE 6

Comparison of Z isomer of Compound (10) (API) from Different Batches

| | | Z isomer (by HPLC) | | | | | | | | |
|---|---|---|---|---|---|---|---|---|---|---|
| | | Product | | | | E Isomer impurities | | | | |
| Batch No. | Notes | Z-trans-1 | Z-trans-2 | Z-Cis-1 | Z-Cis-2 | E-trans-1 | E-trans-2 | E-Cis-1 | E-Cis-2 | Sum of impurities |
| 1 | Reference standard Starting material from TCI | 42.9% | 46.07% | 3.63% | 3.34% | 3.19% | 3.19% | 0.42% | 0.44% | 7.24% |
| 2 | From crude Compound (9) Salt | 47.39% | 48.37% | 1.76% | 0.17% | 0.88% | 0.88% | ND | 1.41% | 3.17% |

TABLE 6-continued

Comparison of Z isomer of Compound (10) (API) from Different Batches

| | | Z isomer (by HPLC) | | | | | | | | |
|---|---|---|---|---|---|---|---|---|---|---|
| | | Product | | | | E Isomer impurities | | | | |
| Batch No. | Notes | Z-trans-1 | Z-trans-2 | Z-Cis-1 | Z-Cis-2 | E-trans-1 | E-trans-2 | E-Cis-1 | E-Cis-2 | Sum of impurities |
| 3 | toCompound (10) Without distillation and recrystallization From crude Compound (9) Salt to Compound (10) Without distillation and recrystallization | 46.86% | 47.82% | 2.19% | 0.40% | 1.07% | 1.07% | ND | 1.64% | 3.78% |
| 4 | Compound (6) from TCI | 42.97% | 46.41% | 3.33% | 3.19% | 3.27% | 3.27% | 0.33% | 0.49% | 7.36% |
| 5 | Purification of Compound (6) with distillation and salt formation, then recrystallization (two times) | 48.21% | 49.11% | 0.87% | 0.79% | 0.94% | 0.94% | 0.04% | 0.03% | 1.95% |
| 6 | Purification of Compound (6) with distillation and salt formation, then recrystallization(one time) | 47.96% | 49.04% | 0.96% | 0.84% | 1.09% | 1.09% | 0.07% | 0.04% | 2.29% |
| 7 | Purification of Compound (6) with distillation and salt formation | 47.03% | 48.55% | 1.55% | 1.42% | 1.23% | 1.23% | 0.15% | 0.06% | 2.67% |
| 8 | Distilled products (Compound (6) as raw material Without salt formation and recrystallization | 44.92% | 46.25% | 3.63% | 3.50% | 1.36% | 1.36% | 0.25% | 0.09% | 3.06% |
| 9 | Without distillation Purification of Compound (6) with salt formation, then recrystallization (MeOH 0.5 vol/water 4 vol) | 47.70% | 48.70% | 1.11% | 1.03% | 1.22% | 1.22% | 0.08% | 0.05% | 2.57% |
| 10 | Without distillation Purification of Compound (6) with salt formation, then recrystallization (95% EtOH, 0.5 vol/water, 4 vol) | 47.40% | 48.70% | 1.22% | 1.08% | 1.35% | 1.35% | 0.09% | 0.05% | 2.84% |
| 11 | Without distillation Purification of Compound (6) with salt formation, then recrystallization (IPA 0.5 vol/water 4 vol) | 47.38% | 48.26% | 1.16% | 1.07% | 1.75% | 1.75% | 0.20% | 0.16% | 3.86% |

Example 14: Summary of Synthetic Route for Formation of Compound (10)

Table 7 provides a summary of the synthetic route for Compound (10):

TABLE 7

Summary of the Synthetic Route for Compound (10)

| Batch No | Steps | Product | Scale (g) | Yield (%) | Purity | Appearance |
|---|---|---|---|---|---|---|
| 1 | 1, 2&3 (one-pot reaction) | Compound (3) | 650 | ~61% | 97.3% (HPLC) | Compound (1): Light yellow oil<br>Compound (2): Light yellow oil<br>Compound (3): Off white solid<br>Note: one-pot reaction |
| 2 | 4 | Compound (4) | 150 | ~100% | ~95% (TLC)<br>~80% (HPLC 210 nm) | Light red oil |
| 3 | Side chain | Compound (5) | 84 | ~100% | 97.1% (GC) | Colourless oil |
| 4 | | | 63 | ~100% | 94.0% (GC) | Colourless oil |
| 5 | 5 | Compound (7) | 123 | ~100% | 78.7%(GC) | Light yellow oil |
| 6 | | | 190 | ~100% | 85.8%(GC) | Light yellow oil |
| 7 | 6 | Compound (6) | 209 | NA | Compound (6) crude: ~82% (cis-cis + cis-tran) | Light brown oil |
| | | | | ~69% | Distillated Compound (6): 81.9% GC (cis-cis + cis-trans) | Light yellow oil |
| 8 | | | 164 | NA | Compound (6) crude: ~80% (cis-cis + cis-trans) | Light brown oil |
| | | | | ~70% | Distillated Compound (6): ~82.7% GC (cis-cis + cis-trans) | Light yellow oil |
| 9 | 7 | Compound (8) Crude | 86 | ~100% | ~97% GC (cis-cis + cis-trans) | Light yellow oil |
| 10 | | | 113 | ~100% | 93.5% GC (cis-cis + cis-trans) | Light yellow oil |
| 11 | 8 | Compound (9) | 80 | 68.2% | NA | White powder |
| 12 | | Salt | 105 | 68.5% | NA | White powder |
| 13 | 9 | Compound (8) | 80 | ~100% | NA | Light yellow oil |
| 14 | | Pure | 110 | ~100% | NA | Light yellow oil |
| 15 | 10 | Compound (10) (API) | 43 | 93.5% | Chemical purity: 99.5% GC<br>Z isomer: 97.5%, total E isomer impurities: 2.5% HPLC | Light yellow oil |
| 16 | | | 59 | 94.9% | Chemical purity: 99.6%<br>Z isomer: 99.06%, total E isomer impurities: 0.94% | Light yellow oil |

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

What is claimed is:

1. A method of preparing a compound of formula (I)

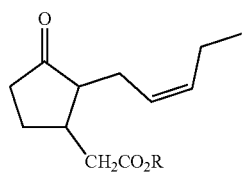

(I)

wherein R is a heteroaryl group, the method comprising (a) treating jasmonic acid salt (9)

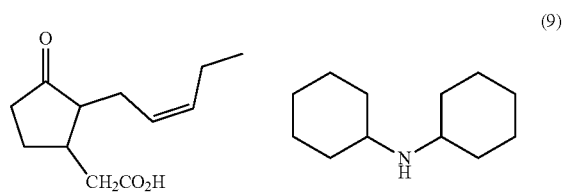

(9)

with an acid at a temperature of from about 0° C. to about 15° C. to provide Compound (8),

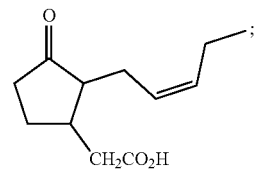

(8)

and
- (b) reacting Compound (8) with a hydroxylheteroaryl to provide the compound of formula (I).

2. The method of claim 1, wherein said hydroxylheteroaryl of Step (b) is 8-hydroxyquinoline.

3. The method of claim 1, wherein said compound of formula (I) is obtained with a yield of at least 99.0%, or at a purity of about 99.6%.

4. The method of claim 1, wherein said compound of formula (I) contains less than 5% of E isomer.

5. The method of claim 1, wherein the compound of formula (I) is obtained with a Z isomer in the amount of about 99.0%.

6. The method of claim 1, wherein said acid is HCl in water.

7. The method of claim 1, wherein said jasmonic acid salt (9) is prepared by
- (a) hydrolyzing a compound (6)

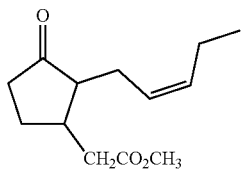

(6)

with a base to form a crude compound (8)

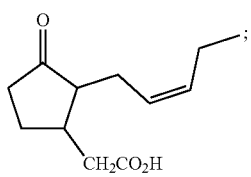

(8)

and
- (b) reacting the crude compound (8) with dicyclohexylamine at a temperature of from about 0° C. to about 10° C. in an organic solvent to form jasmonic acid salt (9).

8. The method of claim 7, wherein said base is LiOH in water.

9. The method of claim 7, wherein said organic solvent comprises ethyl acetate, heptane, or a mixture of ethyl acetate and n-heptane.

10. The method of claim 7, wherein said crude compound (8) is obtained at a purity of about 93.0%.

11. The method of claim 7, wherein said compound (6) is prepared by treating Compound (7)

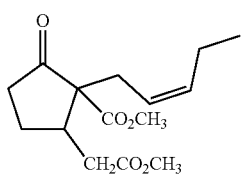

(7)

with LiCl in a solvent at a temperature of from about 120° C. to about 130° C.

12. The method of claim 11, wherein said solvent is a mixture of water and an organic solvent.

13. The method of claim 11, wherein said compound (7) is prepared by reacting compound (4)

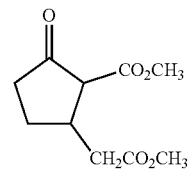

(4)

with 1-bromo-2-pentene in the presence of $Cs_2CO_3$.

14. The method of claim 1, wherein said compound of formula (I) is Compound (10)

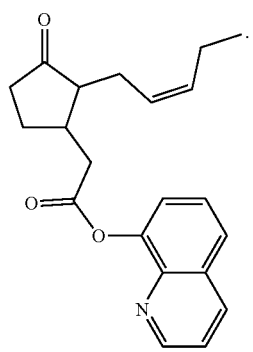

(10)

15. A method of preparing jasmonic acid salt (9)

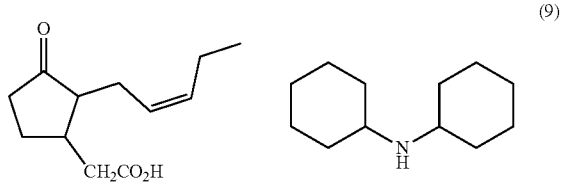

(9)

the method comprising
- (a) hydrolyzing Compound (6)

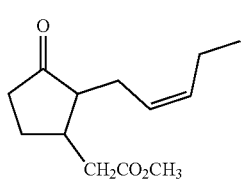

(6)

with a base at a temperature of from about 20° C. to about 30° C. to form a crude Compound (8)

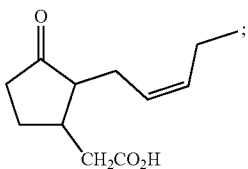
(8)

and
(b) reacting the crude compound (8) with dicyclohexylamine at a temperature of from about 0° C. to about 10° C. in an organic solvent to provide jasmonic acid salt (9).

16. The method of claim 15, wherein said base is LiOH in water.

17. The method of claim 15, wherein said organic solvent comprises ethyl acetate, heptane, or a mixture of ethyl acetate and n-heptane.

18. The method of claim 15, wherein said crude compound (8) is obtained at a purity of about 93.0%.

19. The method of claim 15, wherein said compound (6) is prepared by treating compound (7)

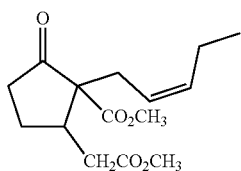
(7)

with LiCl in a solvent at a temperature of from about 120° C. to about 130° C.

20. The method of claim 19, wherein said solvent is a mixture of water and an organic solvent.

21. The method of claim 19, wherein said compound (7) is prepared by reacting compound (4)

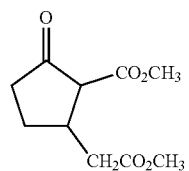
(4)

with 1-bromo-2-pentene in the presence of $Cs_2CO_3$.

* * * * *